United States Patent [19]
Abe et al.

[11] Patent Number: 4,813,928
[45] Date of Patent: Mar. 21, 1989

[54] NOZZLE FOR TISSUE ADHESIVE

[75] Inventors: Michiro Abe, Toride; Masanobu Iwasa, Osaka, both of Japan

[73] Assignees: Hoechst Japan Limited, Tokyo; Nissho Corporation, Osaka, both of Japan

[21] Appl. No.: 36,523

[22] Filed: Apr. 9, 1987

[30] Foreign Application Priority Data

Apr. 23, 1986 [JP] Japan .............................. 61-61152[U]

[51] Int. Cl.$^4$ ............................................... A61M 5/00
[52] U.S. Cl. ...................................... 604/49; 604/264; 604/275
[58] Field of Search ............... 604/264, 272, 280, 281, 604/239, 49, 275, 279, 117; 222/74, 566–568

[56] References Cited

U.S. PATENT DOCUMENTS

| | | | |
|---|---|---|---|
| 20,061 | 8/1936 | Kirk | 604/275 |
| 1,125,887 | 1/1915 | Schimmel | 604/117 |
| 2,850,014 | 9/1958 | Ginsburg | 604/272 |
| 2,922,420 | 1/1960 | Cheng | 604/272 |
| 3,330,268 | 7/1967 | Goldsmith | 604/272 |
| 3,439,675 | 4/1969 | Cohen | 604/275 |
| 3,525,339 | 8/1970 | Halligan | 604/264 |
| 3,958,557 | 5/1976 | Sharp et al. | 604/280 |
| 4,236,520 | 12/1980 | Anderson | 604/264 |
| 4,432,758 | 2/1984 | Finegold | 604/264 |
| 4,573,979 | 3/1986 | Blake | 604/275 X |
| 4,631,055 | 12/1986 | Redl et al. | 604/82 |

*Primary Examiner*—Dalton L. Truluck
*Attorney, Agent, or Firm*—Armstrong, Nikaido, Marmelstein & Kubovcik

[57] ABSTRACT

A syringe-needle-like nozzle for tissue adhesive comprising a hub and a deformable cannula without a bevel, the cannula being made of high-ductile metallic material for medical use and fixed in the hub. The nozzle of the present invention is satisfactorily applicable in tissue adhesive injection to complex regions or small regions in organism. Further, there can be carried out the injection of tissue adhesive to different regions by means of suitable deformation of the nozzle shape.

2 Claims, 1 Drawing Sheet

NOZZLE FOR TISSUE ADHESIVE

BACKGROUND OF THE INVENTION

The present invention relates to a freely deformable nozzle for tissue adhesive, and more particularly to a nozzle to be used for injection of an tissue adhesive in surgical operation or therapy for organism. The nozzle has deformability so as to be suitably used in complex regions in an organism.

Hitherto, in the treatment for regions under surgical operation or for affected surfaces of an organism, there is generally used gauze wetted with medical fluid.

Further, as a method for anastomosis and hemostasis after surgical operation, there has been recently developed a new method using tissue adhesive composed mainly of fibrinogen instead of using suture. In the above method, since the tissue adhesive is generally in liquid form, a conventional syringe is usually used in injecting the adhesive to required regions in organism.

However, there exist problems in using the above mentioned gauze that, although the use of gauze is suitable for treatment of easily accessible regions, it is difficult to use gauze for the inside of skull or for medial tissue such as digestive organ and wind pipe, and that it is not a satisfactory measure to use gauze in such case as operation where rapid anastomosis and hemostasis are required.

The method using the tissue adhesive by conventional syringe needles also has a problem that the bevel (sharp end) of syringe needle might damage tissue. As an alternative, there is available a needle formed in a particular shape such as conventional dental syringe needles, but it is difficult to apply the above conventional dental syringe needle to complex and complicated regions in an organism such as the inside of the cranium, the deep region in the auditory meatus and the inner surface of the digestive tract.

The present invention was made based on a result of vigorous researches and investigations to solve the above mentioned problems in the conventional methods. An object of the present invention is to provide a nozzle for tissue adhesive which has deformability so as to be used in complex regions of an organism and enables rapid anastomosis and hemostasis as the result.

SUMMARY OF THE INVENTION

In accordance with the present invention, there is provided a syringe-needle-like nozzle for tissue adhesive comprising a hub and a deformable cannula without the bevel, the cannula being made of high-ductile metalic material for medical use and fixed in the hub.

Since a nozzle of the present invention is deformable, the shape thereof can be changed freely and suitably for the region in which the nozzle is used. Therefore, even in being used in complex regions, the end of the nozzle can be easily introduced to the region and the tissue adhesive can be easily applied to the region, by means of suitable deformation of the nozzle shape. Further, in operation where two or more nozzles having different shapes are usually required, the tissue adhesive can be applied to different regions using only one nozzle by means of changing the shape thereof.

DETAILED DESCRIPTION

There is now explained a nozzle of the present invention based on the drawings.

Figure 1:
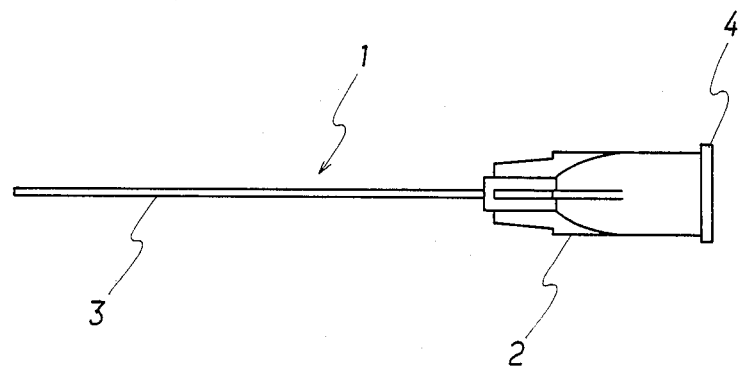
FIG. 1 is a front view of an embodiment of a nozzle of the present invention.

FIG. 1 is a front view of an embodiment of a nozzle of the present invention. As shown in FIG. 1, a nozzle 1 of the present invention comprises a hub 2 and a cannula 3. The hub 2, which is similar to that of the ordinary syringe needle, is made of metal or thermoplastic resin such as polypropylene, polyethylene, methylpentene polymer and polycarbonate. On one side of the hub 2, there is formed an engaging part 4 for the connection with a syringe, and on the other side thereof the cannula 3 is inserted and fixed therein.

As the cannula 3, there can be used a tube obtained in a process of manufacturing syringe needle before it is sharpened, because the cannula 3 does not have the bevel (sharp end). When the above obtained tube is undesirably hard, it is annealed to be softened before being used.

As high-dutile metalic material for medical use which is used for the cannula 3, there can be used stainless steel, tantalum, titanium-tantalum alloy or the like. The stainless steel is preferable because it is more economical than the other material.

Next, there is explained the usage of the nozzle of the present invention.

Figure 2:
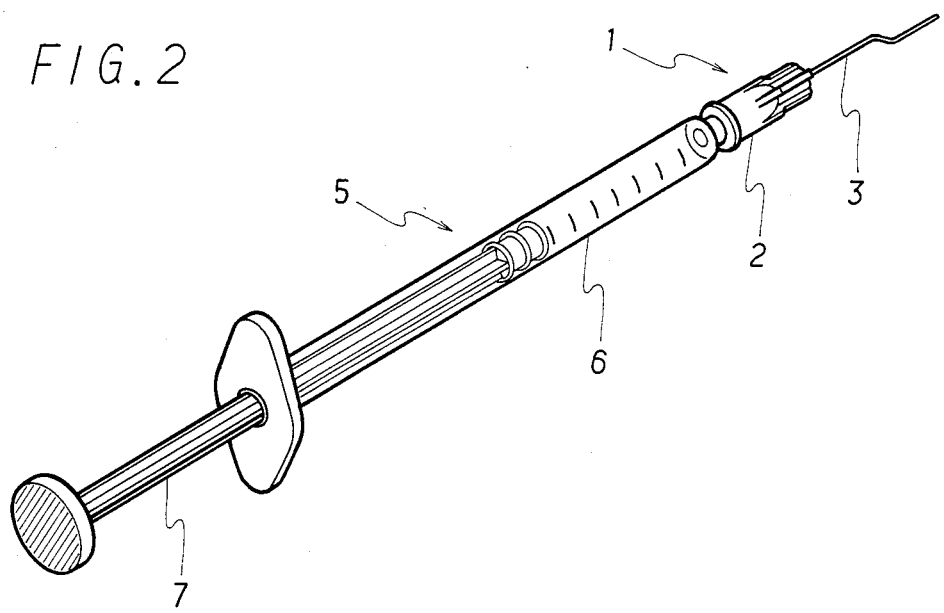
FIG. 2 is a perspective view of a nozzle of the present invention fixed to a syringe.

FIG. 2 is a perspective view of the above mentioned nozzle fixed to a syringe. When the nozzle 1 of the present invention is used, it is firstly fixed to the syringe 5 by means of connecting the engaging part 4 of the nozzle 1 to a barrel 6 of the syringe 5 as shown in FIG. 2. Next, the cannula 3 is deformed to suitable shape corresponding to a region whereto tissue adhsive is applied, then a plunger 7 is pulled to draw up a component of tissue adhesive comprising fibrinogen concentrate solution into the syringe 5. The end of the cannula 3 is introduced to the region and finally the plunger 7 is pushed by finger. Thus the fibrinogen concentrate solution is surely applied to the region requiring adhesion. Then the other component of tissue adhesive comprising thrombin solution is drawn up into another syringe and applied onto the region whereto the fibrinogen concentrate solution has been applied. The mixed tissue adhesive components become immediately glutinous and glue up the tissue in a few minutes.

Next, there is explained an example where the nozzle of the present invention is applied to meningioma-ectomy. As the final step of meningioma-ectomy, suture of dura is carried out then cranium is closed. In that step, suture is sometimes defficult when the edge of cranial bone near incised region of dura obstructs it. The edge of cranial bone is gnawed off with forceps or the like, if it is practicable. But if it is not practicable, it is a conventional manner that cranium is closed without suture of dura while cerebrospinal fluid is allowed to flow out.

Tissue adhesive such as fibrin adhesive, when applied to the above case, can glue the incised region of dura and prevent a cerebrospinal fluid from flowing out. However, the dura, to which tissue adhesive should be applied, is hidden by cranial bone and is not easily accessible. Further, the cavity between dura and cranial bone is very narrow. Because of the above reasons, it is very difficult to apply tissue adhesive to the incised region of dura with conventional syringe needles.

However, when a nozzle of the present invention is used, the nozzle can be easily deformed to a shape suitable to the region and by virtue of this advantage the incised region of dura can be glued surely and safely.

The nozzle of the present invention is satisfactorily applicable to the injection of tissue adhesive to complex regions or small regions in organism. For example, the nozzle of the present invention can be effectively used in adhesion of periosteum valve of oral mucus membrane, hemostasis of dura or of deep region in cranium, adhesion of nerves, forming tympanum by adhesion of small auditory bone, connection of micro blood vessels, anastomosis of lumen tissue (especially rear side tissue) such as digestive track, and the like. Generally, the nozzle of the present invention can be effectively used when tissue adhesive is applied in adhesive fixation of tissue, local hemostasis, filling to close defective regions of tissue, protection of wound or the like.

As is described hereinbefore, since the nozzle of the present invention is deformable, the shape thereof can be changed freely and suitably for the region to which tissue adhesive is applied. Therefore, even in being used in complex regions, the end of the nozzle can be easily introduced to the region and the tissue adhesive can be easily injected to the region. Further, there can be carried out the injection of tissue adhesive to different regions by only one nozzle.

What we claim is:

1. A device for applying tissue adhesive into a hard-to-access region of an organism comprising a syringe for containing tissue adhesive and a nozzle, said nozzle comprising a hub adapted to be engaged to the syringe, and a stainless steel cannula having a smooth distal end perpendicular to its axis for insertion into the organism and fixed at its other end into the hub, said cannula being softened by annealing and being freely deformable to a shape suitable for introduction into the hard-to-access region.

2. A method for applying tissue adhesive from a syringe into a hard-to-access region of an organism which comprises:
   utilizing as a nozzle for the syringe a stainless steel cannula having a hub at one end engaged to the syringe and a smooth distal end perpendicular to the axis of the cannula, said cannula being softened by annealing and capable of being freely deformed;
   deforming the cannula to a shape suitable for introduction into the hard-to-access region;
   inserting the distal end of the cannula into the hard-to-access region; and
   applying the tissue adhesive by means of the nozzle from the syringe to the hard-to-access region.

* * * * *